(12) United States Patent
Kang

(10) Patent No.: US 12,017,010 B2
(45) Date of Patent: Jun. 25, 2024

(54) SOUND CONTROL SYSTEM AND METHOD FOR DENTAL TREATMENT

(71) Applicant: HEALING SOUND CO., LTD., Seoul (KR)

(72) Inventor: Jun Gu Kang, Seoul (KR)

(73) Assignee: HEALING SOUND CO., LTD., Seoul (KR)

( * ) Notice: Subject to any disclaimer, the term of this patent is extended or adjusted under 35 U.S.C. 154(b) by 248 days.

(21) Appl. No.: 17/782,655

(22) PCT Filed: Aug. 20, 2020

(86) PCT No.: PCT/KR2020/011073
§ 371 (c)(1),
(2) Date: Jul. 5, 2022

(87) PCT Pub. No.: WO2021/112373
PCT Pub. Date: Jun. 10, 2021

(65) Prior Publication Data
US 2022/0387747 A1    Dec. 8, 2022

(30) Foreign Application Priority Data
Dec. 5, 2019   (KR) .......................... 10-2019-0160886

(51) Int. Cl.
*A61M 21/02*   (2006.01)
*A61C 19/00*   (2006.01)
(Continued)

(52) U.S. Cl.
CPC ............. *A61M 21/02* (2013.01); *A61C 19/00* (2013.01); *G06F 3/165* (2013.01); *G10L 17/00* (2013.01);
(Continued)

(58) Field of Classification Search
CPC ........... G10L 17/00; G10L 2021/02163; G10L 21/0232; H04R 1/08; H04R 1/1008;
(Continued)

(56) References Cited

U.S. PATENT DOCUMENTS 7,113,201 B1 *   9/2006   Taylor ...................... H04N 7/15
348/E7.083
7,117,157 B1 *   10/2006  Taylor ..................... G06F 3/167
704/E15.041
(Continued)

FOREIGN PATENT DOCUMENTS

KR      10-0787994 B1    12/2007
KR      10-1015318 B1    2/2011
(Continued)

OTHER PUBLICATIONS

International Search Report for PCT/KR2020/011073 mailed Nov. 25, 2020 from Korean Intellectual Property Office.

*Primary Examiner* — Lun-See Lao
(74) *Attorney, Agent, or Firm* — Revolution IP, PLLC

(57) ABSTRACT

A sound control system for dental treatment, includes: ear-worn speakers equipped to be worn by a patient in the dentist; a microphone that converts, into an electrical signal, a sound including the voice of a medical staff in charge of the patient; a voice recognition module for recognizing the voice of the medical staff in charge from an electrical sound signal input from the microphone; a sound source module that stores a plurality of sound sources for mental and physical stability of the patient; a user interface including a sound source selection unit that allows the patient to select a play sound source provided via the ear-worn speakers from among the plurality of sound sources; and an output signal generation module for generating an output sound signal output via the ear-worn speakers.

12 Claims, 3 Drawing Sheets

(51) Int. Cl.
  *A61M 21/00* (2006.01)
  *G06F 3/16* (2006.01)
  *G10L 17/00* (2013.01)
  *G10L 21/0216* (2013.01)
  *G10L 21/0232* (2013.01)
  *H04R 1/08* (2006.01)
  *H04R 1/10* (2006.01)
  *H04R 3/04* (2006.01)

(52) U.S. Cl.
  CPC ............ *G10L 21/0232* (2013.01); *H04R 1/08* (2013.01); *H04R 1/1008* (2013.01); *H04R 1/1041* (2013.01); *H04R 3/04* (2013.01); *A61C 2203/00* (2013.01); *A61M 2021/0027* (2013.01); *A61M 2205/3375* (2013.01); *G10L 2021/02163* (2013.01); *H04R 2410/03* (2013.01); *H04R 2430/01* (2013.01)

(58) Field of Classification Search
  CPC ............ H04R 1/1041; H04R 2410/03; H04R 2430/01; H04R 3/04; H04R 1/1083; H04R 2420/07; A61C 19/00; A61C 2203/00; A61C 1/081
  USPC ................. 381/74, 312, 56–58; 700/94
  See application file for complete search history.

(56) References Cited

U.S. PATENT DOCUMENTS

| | | | |
|---|---|---|---|
| 2004/0107080 A1* | 6/2004 | Deichmann | A61F 11/08 703/6 |
| 2004/0234089 A1* | 11/2004 | Rembrand | H04R 25/30 381/317 |
| 2015/0195641 A1* | 7/2015 | Di Censo | H04R 1/1083 381/71.6 |
| 2015/0304761 A1* | 10/2015 | Montazemi | H04R 1/1083 381/72 |
| 2017/0347178 A1* | 11/2017 | Masaki | H04R 1/1091 |

FOREIGN PATENT DOCUMENTS

| | | |
|---|---|---|
| KR | 10-2014-0022163 A | 2/2014 |
| KR | 10-1647974 B1 | 8/2016 |
| KR | 10-1958839 B1 | 7/2019 |
| KR | 10-2006250 B1 | 8/2019 |

* cited by examiner

SOUND CONTROL SYSTEM AND METHOD FOR DENTAL TREATMENT

TECHNICAL FIELD

The present invention relates to a dental treatment technology, and more particularly, to a sound control system and method for dental treatment, whereby unnecessary noise is blocked and communication between a patient and a medical staff in charge is facilitated during dental treatment.

BACKGROUND ART

It is very significant to create a comfortable and comfortable environment for treating patients. A quiet environment may be provided to a patient depending on how a disease is treated, whereas in the dental field, sharp and high-frequency noise generated during a treatment process may create discomfort or fear in the patient. However, measures to protect patients exposed to such high-frequency noise are insufficient.

Meanwhile, an active noise control technology is a technology, whereby ambient noise is received through a microphone separately attached to a headphone or an earphone and destructive interference for cancelling the noise is generated in a noise cancelling circuit, thereby blocking noise. In the related art, the active noise control technology is applied to the headphone or earphone and thus used only for multimedia viewing, and the development of technology to be applied to other environments has not been largely accomplished.

DETAILED DESCRIPTION OF THE INVENTION

Technical Problem

The present invention provides a sound control system and method for dental treatment, whereby unnecessary noise is blocked and communication between a patient and a medical staff in charge is facilitated during dental treatment.

Technical Solution

According to an aspect of the present invention, there is provided a sound control system for dental treatment, the sound control system including ear-worn speakers equipped to be worn by a patient in the dentist; a microphone that converts, into an electrical signal, a sound including a voice of a medical staff in charge of the patient; a voice recognition module for recognizing the voice of the medical staff in charge from an electrical sound signal input from the microphone; a sound source module that stores a plurality of sound sources for mental and physical stability of the patient; a user interface including a sound source selection unit that allows the patient to select a play sound source provided via the ear-worn speakers from among the plurality of sound sources; and an output signal generation module for generating an output sound signal output via the ear-worn speakers, wherein, when the voice of the medical staff in charge is recognized from the voice recognition module while generating the play sound source as the output sound signal, the output signal generation module generates the output sound signal including a voice signal of the medical staff in charge.

According to another aspect of the present invention, there is provided a sound control method for dental treatment using a sound control system for dental treatment including ear-worn speakers equipped to be worn by a patient in the dentist, a microphone that converts, into an electrical signal, a sound including a voice of a medical staff in charge of the patient, a voice recognition module for recognizing the voice of the medical staff in charge from an electrical sound signal input from the microphone, a sound source module that stores a plurality of sound sources for mental and physical stability of the patient, a user interface including a sound source selection unit that allows the patient to select a play sound source provided via the ear-worn speakers from among the plurality of sound sources, and an output signal generation module for generating an output sound signal output via the ear-worn speakers, the sound control method including: a sound source setting operation in which in which a play sound source provided to the ear-worn speakers is selected from among the plurality of sound sources through the user interface; a sound source outputting operation in which the play sound source selected in the sound source setting operation is output to the ear-worn speakers through the output signal generation module; a voice recognition checking operation in which it is checked whether the voice of the medical staff in charge is recognized through the voice recognition module while the play sound source is output in the sound source outputting operation; and a voice signal outputting operation in which the voice signal of the medical staff in charge is output to the ear-worn speakers through the output signal generation module when it is checked that the voice of the medical staff in charge is recognized in the voice recognition checking operation.

Effects of the Invention

According to the present invention, all of the objectives of the present invention described above can be achieved. In detail, because a sound control system for dental treatment, the sound control system including ear-worn speakers equipped to be worn by a patient in the dentist, a microphone that converts, into an electrical signal, a sound including a voice of a medical staff in charge of the patient, a voice recognition module for recognizing the voice of the medical staff in charge from an electrical sound signal input from the microphone, a sound source module that stores a plurality of sound sources for mental and physical stability of the patient, a user interface including a sound source selection unit that allows the patient to select a play sound source provided via the ear-worn speakers from among the plurality of sound sources, and an output signal generation module for generating an output sound signal output via the ear-worn speakers, wherein, when the voice of the medical staff in charge is recognized from the voice recognition module while generating the play sound source as the output sound signal, the output signal generation module generates the output sound signal including a voice signal of the medical staff in charge and a sound control method for dental treatment using the sound control system for dental treatment are provided, during dental treatment, the patient is able to receive dental treatment in a state where the patient is mentally physically relaxed while hearing the patient's preferred sound source with reduced noise, and the voice of the medical staff in charge can be smoothly transmitted to the patient during a treatment process, and dental treatment can be effectively performed.

In addition, because the patient is able to generate a mixed sound source suitable for his/her own taste by mixing a plurality of sound sources and to hear the mixed sound source during dental treatment, the patient can receive dental treatment more effectively.

MODE OF THE INVENTION

Hereinafter, the configuration and operation of embodiments of the present invention will be described in detail with reference to the accompanying drawings.

Figure 1:
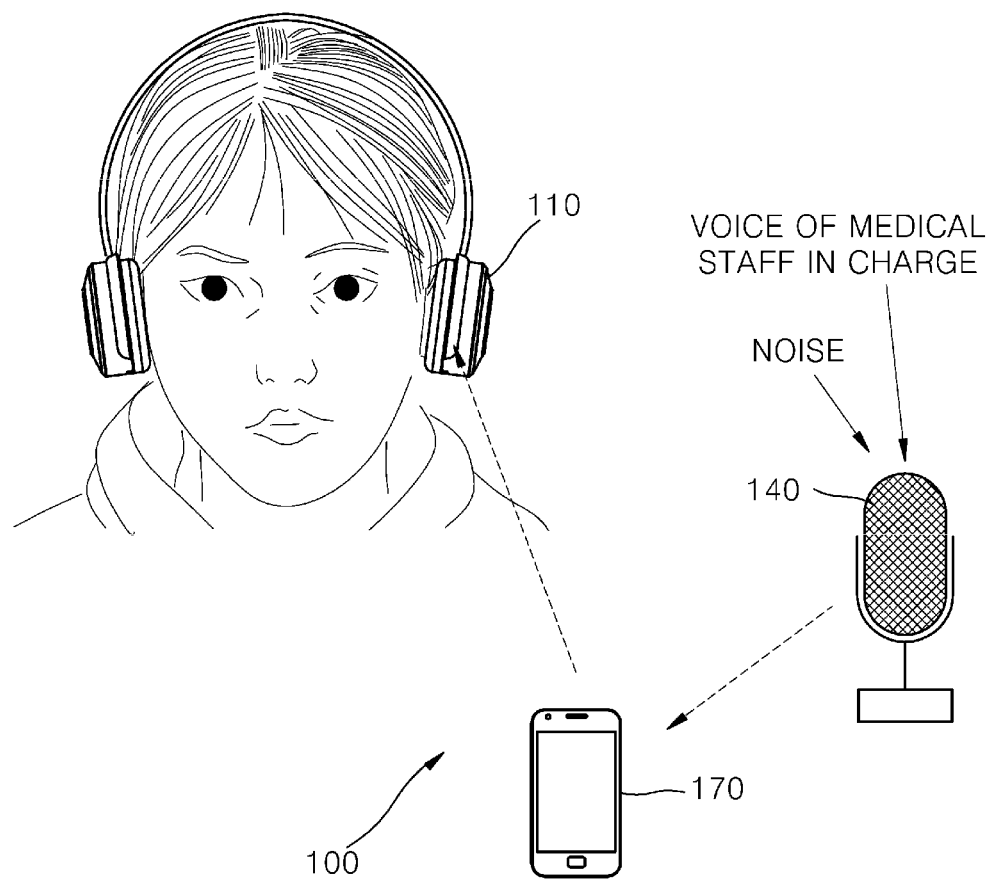
FIG. 1 is a view schematically illustrating elements of a sound control system for dental treatment according to an embodiment of the present invention.
Figure 2:
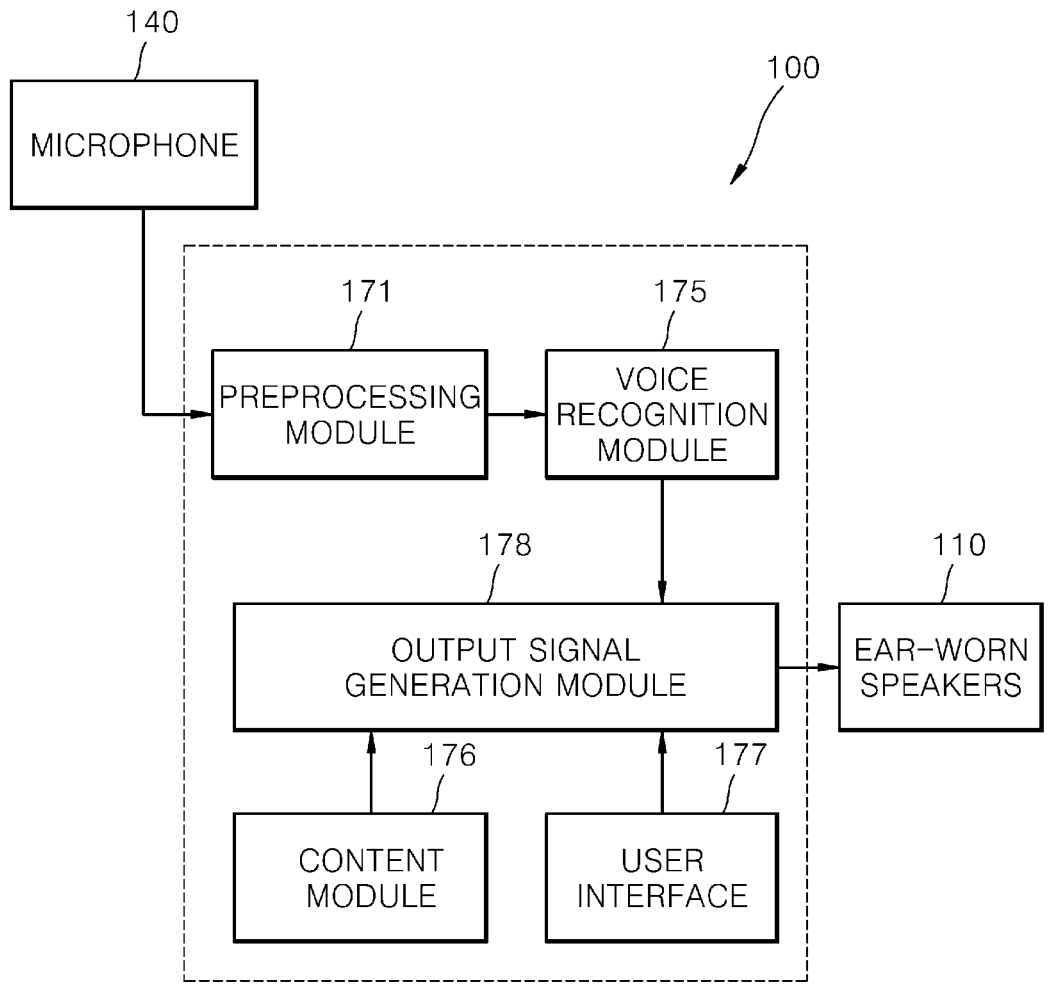
FIG. 2 is a block diagram of the sound control system for dental treatment shown in FIG. 1 according to an embodiment of the present invention.

FIG. 1 is a view schematically illustrating elements of a sound control system for dental treatment according to an embodiment of the present invention, and FIG. 2 is a block diagram of the sound control system for dental treatment shown in FIG. 1 according to an embodiment of the present invention Referring to FIGS. 1 and 2, a sound control system 100 for dental treatment according to an embodiment of the present invention includes ear-worn speakers 110 equipped to be worn by a patient, a microphone 140 that converts a sound including the voice of a medical staff in charge of the patient into an electrical signal, and a control device 170 that processes the electrical sound signal input from the microphone 140 and outputs an electrical sound signal corresponding to sound necessary for the patient to the ear-worn speakers 110.

The ear-worn speakers 110 convert the electrical sound signal transmitted from the control device 170 into a sonic wave so that the patient can hear it. To this end, the ear-worn speakers 110 are connected to the control device 170 so as to be capable of communicating with the control device 170 by using various shapes of wired/wireless communication technologies, and in the present embodiment, it will be described that the ear-worn speakers 110 are connected to the control device 170 using a short-range wireless communication technology such as Bluetooth. In the present embodiment, it will be described that, as shown in FIG. 1, the ear-worn speakers 110 have the shape of headphones but unlike this, the shape of earphones, and this also belongs to the scope of the present invention. The patient hears only the patient's desired sound instead of ambient unnecessary sound (noise) through the ear-worn speakers 110.

The microphone 140 converts ambient sound including the voice of the medical staff in charge of the patient into an electrical signal to transmit the electrical signal to the control device 170. To this end, the microphone 140 is connected to the control device 170 so as to be capable of communicating with the control device 170 by using various shapes of wired/wireless communication technology, and in the present embodiment, it will be described that the microphone is connected to the control device 170 by using a short-range wireless communication technology, such as Bluetooth. In the present embodiment, it will be described that the microphone 140 is worn by the medical staff (doctor) who treats the patient during dental treatment and used. However, the present invention is not limited thereto, and the microphone 140 may be properly placed in the vicinity of the patient and the medical staff and used. Also, in the present invention, it will be described that the microphone 140 is an additional device separated from the ear-worn speakers 110 and the control device 170, however, unlike this, the microphone 140 may be integrally coupled to the ear-worn speakers 110, or a microphone installed in the control device 170 may be used, and this also belongs to the scope of the present invention. Although not shown, a filter for filtering a sound signal in a required frequency band is together installed in the microphone 140 so that the filtered sound signal may be transmitted to the control device 170, and this also belongs to the scope of the present invention.

The control device 170 processes the electrical sound signal input from the microphone 140 and outputs an electrical sound signal corresponding to sound necessary for the patient to the ear-worn speakers 110. In the present embodiment, it will be described that the control device 170 is a personal portable communication terminal device such as a smartphone held by the patient, however, the present invention is not limited thereto, and the control device 170 may be an additional device provided by a hospital including a tablet personal computer (PC) that is not the patient's thing, and this also belongs to the scope of the present invention.

Referring to FIG. 2, the control device 170 includes a preprocessing module 171 for preprocessing the electric sound signal transmitted from the microphone 140 and outputting a preprocessed signal, a voice recognition module 175 for recognizing voice from the preprocessed signal output from the preprocessing module 171 and outputting a voice recognition signal, a sound source module 176 in which sound content including a plurality of sound sources are stored, a user interface 177 for connecting the control device 170 and a user of the control device 170, and an output signal generation module 178 for generating an output signal based on the plurality of sound sources output from the sound source module 176 and the voice recognition signal output from the voice recognition module 175 in response to setting matters by the user interface 177. The elements of the control device 170 including the preprocessing module 171, the voice recognition module 175, the sound source module 176, the user interface 177, and the output signal generation module 178 may be implemented via an application program called application in a terminal device such as a smartphone.

Figure 3:
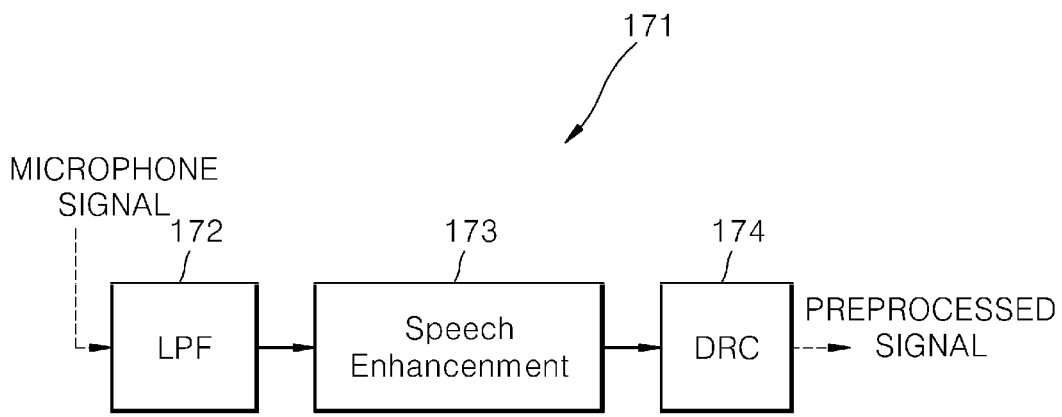
FIG. 3 is a block diagram of the configuration of a preprocessing unit shown in FIG. 2 according to an embodiment of the present invention.

The preprocessing module 171 preprocesses the electric sound signal transmitted from the microphone 140, removes the sound signal unnecessary for the patient, and outputs a preprocessed signal in which the voice signal is reinforced. FIG. 3 is a block diagram illustrating the elements of the preprocessing module 171 according to an embodiment of the present invention. Referring to FIG. 3, the preprocessing module 171 includes a low pass filter (LPF) 172, a speech enhancement 173, and a dynamic range compressor (DRC) 174.

The LPF 172 passes a low-frequency band and blocks a high-frequency band in the electric sound signal transmitted from the microphone 140, thereby reducing or blocking high-frequency noise distributed in a relatively high-frequency band. A primary processed signal passing through the LPF 172 is transmitted to the speech enhancement 173.

The speech enhancement 173 outputs a secondary processed signal in which background noise is estimated from the primary processed signal output from the LPF 172 and is removed. Because the speech enhancement 173 is technology (e.g., speech enhancement technology disclosed in Registration Patent No. 10-1662946) generally used as a signal processing method for improving the performance of a voice recognition or voice communication system, a detailed description thereof will be omitted.

The DRC 174 outputs a third processed signal in which voice intelligibility is enhanced in the secondary processed signal output from the speech enhancement 173 by using a dynamic range compression (DRC) technique. DRC is to reduce a difference in volume sizes between a portion where the volume of a voice signal is large and a portion where the volume of a voice signal is small, so as to increase volume while reducing distortion, and for example, a DRC technique disclosed in Korean Registration Patent No. 10-1981487, may be used.

The voice recognition module 175 recognizes specific voice from the preprocessed signal output from the preprocessing module 171 to output a voice recognition signal. The voice recognition module 175 specifically detects the voice of the medical staff in charge of the patient in a noise environment. In the present embodiment, it will be described that the voice recognition module 175 recognizes the voice of the medical staff in charge of the patient by using a general deep learning technology (e.g., a voice recognition method utilizing a deep learning algorithm disclosed in Korean Patent Laid-open Publication No. 10-2019-0074011).

The sound source module 176 stores sound content including a plurality of sound sources provided to the patient and provides the sound content selected by a user including the patient through the user interface 177 to the output signal generation module 178. The sound source stored in the sound source module 176 includes sound for mental and physical stability of the patient such as rain, wind, thunder, creek, fireplace, waves, and birdsong, and the present invention is not limited thereto, and the sound source stored in the sound source module 176 may be music that may be selected by the patient or the medical staff, or sound content caused by a character that may be selected by the patient or the medical staff, and this also belongs to the scope of the invention. Also, sound source module 176 may be an external application program (e.g., 'Melon' that is a sound source service operated by Kakao Corporation) for providing a sound source streaming service in addition to a sound source module stored in the control device 170, and this also belongs to the scope of the present invention. The sound source stored in the sound source module 176 may include a basic sound source such as rain, wind, thunder, creek, fireplace, waves, and birdsong, and a mixed sound source generated by the user by mixing a plurality of basic sound sources.

Figure 4:
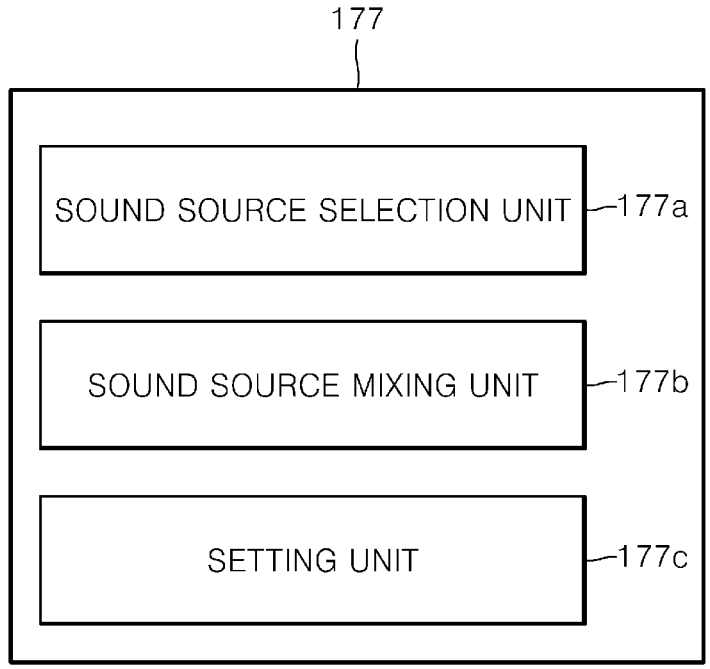
FIG. 4 is a block diagram illustrating the schematic elements of a user interface unit shown in FIG. 2.

The user interface 177 connects between the control device 170 and a user of the control device 170 and the control device 170 so that the user of the control device 170 including the patient may set the control device 170. FIG. 4 illustrates the schematic elements of the user interface 177. Referring to FIG. 4, the user interface 177 includes a sound source selection unit 177a, a sound source mixing unit 177b, and a setting unit 177c.

The sound source selection unit 177a visually provides the plurality of sound sources including the basic sound source and the mixed sound source stored in the sound source module 176 to the user so that the user may select one of the plurality of sound sources. Also, the sound source selection unit 177a may show at least one preferred sound source separately stored by the user in addition to the stored sound sources. The basic sound source or the mixed sound source selected by the sound source selection unit 177a may be directly played so that the patient may hear the sound source during dental treatment. Also, the plurality of sound sources selected by the sound source selection unit 177a may be provided to the sound source mixing unit 177b and used in mixed sound source generation. Although not shown, the sound source selection unit 177a may allow the user to select a character and to select sound content by the character. The sound content by the character may be a description of care and treatment.

The sound source mixing unit 177b may allow the user to generate a mixed sound source by mixing a plurality of sound sources selected by the user from among the plurality of sound sources stored in the sound source module 176 and to add the generated mixed sound source to the sound source module 176 and to store the mixed sound source. The intensity of each of the sound sources selected for mixing may be controlled by the sound source mixing unit 177b. For example, three sound sources, such as the sound of birdsong, the sound of wind, the sound of waves selected by the user from among the plurality of basic sound sources stored in the sound source module 176, may be respectively controlled to a desired intensity and then mixed by the sound source mixing unit 177b so that a mixed sound source may be generated. The mixed sound source generated by the sound source mixing unit 177b may be generated by mixing a plurality of basic sound sources stored in the sound source module 176, but may be generated by adding other basic sound sources to the mixed sound source stored in the sound source module 176 or by mixing a plurality of mixed sound sources, or by additionally mixing at least one basic sound source to the plurality of mixed sound sources.

The setting unit 177c provides a window for setting of the control device 170 to the user of the control device 170. The user sets the filtering frequency of the LPF 172, on/off of a noise reduction function, on/off of sound voice playback, and on/off of a voice automatic detection function.

The output signal generation module 178 generates an output signal based on the sound source output from the sound source module 176 and the voice recognition signal output from the voice recognition module 175 in response to the setting matters by the user interface 177. In detail, the output signal generation module 178 outputs the sound source selected by the user using the sound source module 176 during dental treatment to the ear-worn speaker 110 so that the patient may hear the sound source, and when the voice of the medical staff in charge is recognized by the voice recognition module 175 while the sound source is output during dental treatment, the output signal generation module 178 outputs a voice signal of the medical staff in charge and reduces the volume of the sound of the sound source or eliminates the sound so that the patient may hear the voice of the medical staff through the ear-worn speakers 110. The output signal generation module 178 may generate an output sound signal so that the voice of the medical staff may be transmitted to the patient with the voice of the character selected by the user interface 177. Also, when a time in which the voice of the medical staff is not recognized by the voice recognition module 175 continues for a predetermined amount of time or the medical staff speaks a specific sound (e.g., 'end'), the voice recognition module 175 recognizes it and restores the volume of sound included in the sound source provided by the sound source module 176 to its original state.

The control device may carry out instructions of the medical staff in charge recognized by the voice recognition module 175. For example, when the medical staff in charge asks the control device to increase or decrease the volume of the sound source being output, the control device may control the volume of the sound source being output by recognizing it through the voice recognition module 175. Alternatively, when the medical staff in charge speaks "start treatment", the control device may automatically increase the sound of the sound source, and when the medical staff in charge speaks "finish treatment", the control device may automatically decrease the sound of the sound source. Also, when the medical staff in charge asks the control device to explain treatment through a specific character, the control device may recognize and carry out it.

In the present embodiment, it will be described that the elements of the control device including the preprocessing module 171, the voice recognition module 175, the sound source module 176, the user interface 177 and the output signal generation module 178 is implemented through an application program installed in the control device 170 that is a terminal device such as a smartphone, however, the present invention is not limited thereto. For example, only the user interface 177 is installed in the control device 170, and the remaining elements (the preprocessing module 171, the voice recognition module 175, the sound source module 176, and the output signal generation module 178) may be distributed on the ear-worn speakers 110 or the microphone 140 or may be concentratively installed on any one thereof, and this also belongs to the scope of the present invention.

Although not shown, the output signal generation module 178 may receive an electrical signal from a driving unit of dental power tools such as a dental electric drill, and may output an output sound signal in response to the electrical signal. For example, generally, the number of revolutions of the dental electric drill is controlled by a pedal, and the output signal generation module 178 may receive a signal of the number of revolutions of the motor from the pedal and may increase the volume of the sound of the output sound source as the number of revolutions increases.

Figure 5:
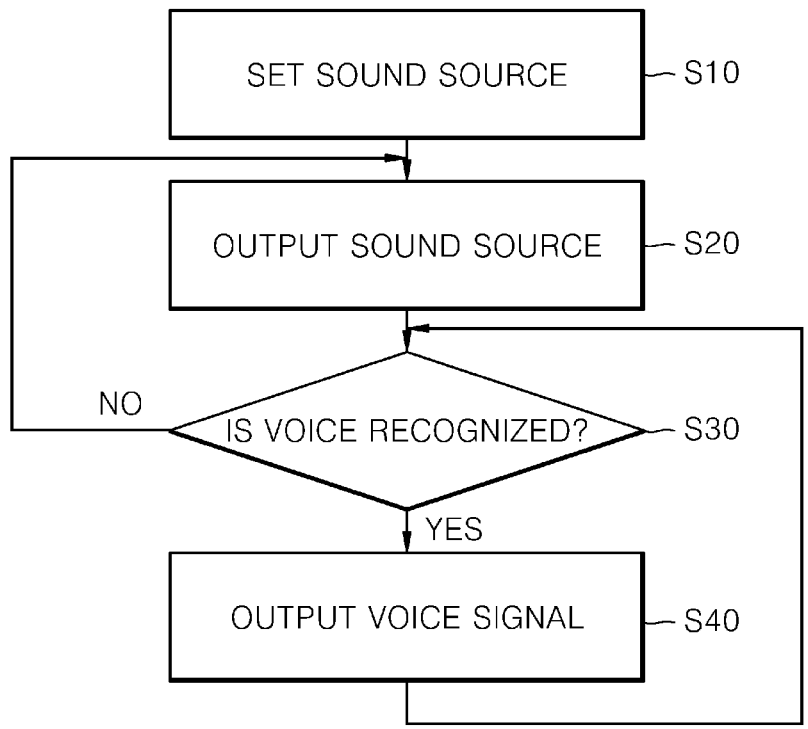
FIG. 5 is a flowchart schematically illustrating a sound control method for dental treatment using the sound control system for dental treatment shown in FIGS. 1 and 2, according to an embodiment of the present invention.

FIG. 5 is a flowchart schematically illustrating a sound control method for dental treatment using the sound control system for dental treatment shown in FIGS. 1 and 2, according to an embodiment of the present invention. Referring to FIG. 5, the sound control method for dental treatment using the sound control system 100 for dental treatment shown in FIGS. 1 and 2 includes a sound source setting operation (S10) in which a sound source is set through the user interface 177, a sound source outputting operation (S20) in which the sound source selected in the sound source setting operation (S10) is output through the output signal generation module 178, a voice recognition checking operation (S30) in which it is checked whether the voice of the medical staff in charge is recognized through the voice recognition module 175 while the sound source is output in the sound source outputting operation (S20), and a voice signal outputting operation (S40) in which the voice signal of the medical staff in charge is output through the output signal generation module 178 when it is checked that the voice of the medical staff in charge is recognized in the voice recognition checking operation (S30).

In the sound source setting operation (S10), a sound source is set through the user interface 177. The sound source setting operation (S10) is performed when the user including the patient sets the sound source stored in the sound source module 176 through the user interface 177 by using the control device 170. In detail, in the sound source setting operation (S10), one sound source to be played during dental treatment may be selected from the plurality of sound sources stored in the sound source module 176. Also, before one sound source to be played is selected, a mixed sound source may be generated by the sound source mixing unit 177b, and the generated mixed sound source may be stored in the sound source module 176, as described above.

In the sound source outputting operation (S20), the sound source selected for play in the sound source setting operation (S10) is output with the volume set to the ear-worn speakers 110 through the output signal generating module 178 so that the sound source selected by the patient is heard during a dental treatment process.

In the voice recognition checking operation (S30), it is checked whether the voice of the medical staff in charge is recognized, through the voice recognition module 175 while the sound source is output in the voice outputting operation (S20). The recognition of the voice of the medical staff in charge is the same as the configuration of the preprocessing module 171 and the voice recognition module 175 described above. When the voice of the medical staff in charge of the patient is not checked in the voice recognition checking operation (S30), the sound source outputting operation (S20) is performed without changes so that the selected sound source is provided to the patient with the set volume. When the voice of the medical staff in charge of the patient is checked in the voice recognition checking operation (S30), a voice signal outputting operation (S40) is performed.

In the voice signal outputting operation (S40), when it is checked that the voice of the medical staff in charge is recognized in the voice recognition checking operation (S30), a voice signal of the medical staff in charge is output to the output signal generation module 178. In detail, when it is checked that the voice of the medical staff in charge is recognized in the voice recognition checking operation (S30), the recognized voice signal of the medical staff in charge is transmitted to the ear-worn speakers 110 through the output signal generation module 178 so that the patient hears the voice of the medical staff in charge through the ear-worn speakers 178. While the voice of the medical staff in charge is output in the voice signal outputting operation (S40), the volume of sound output in the sound source outputting operation (S20) is reduced or eliminated.

While the voice of the medical staff in charge is output in the voice signal outputting operation (S40), the voice recognition operation (S30) is continuously performed, and when the voice of the medical staff in charge is not recognized for a predetermined amount of time in the voice recognition operation (S30) while the voice signal outputting operation (S40) is performed or when a preset specific voice (e.g., 'end') is recognized, the execution of the voice signal outputting operation (S40) is stopped, and the sound source outputting operation (S20) is performed so that the selected sound source instead of the voice of the medical staff is provided to the patient together with its original volume.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A sound control system for dental treatment, the sound control system comprising:
   ear-worn speakers equipped to be worn by a patient in the dentist;
   a microphone that converts, into an electrical signal, a sound including a voice of a medical staff in charge of the patient;
   a voice recognition module for recognizing the voice of the medical staff in charge from an electrical sound signal input from the microphone;
   a sound source module that stores a plurality of sound sources for mental and physical stability of the patient;
   a user interface including a sound source selection unit that allows the patient to select a play sound source provided via the ear-worn speakers from among the plurality of sound sources; and
   an output signal generation module for generating an output sound signal output via the ear-worn speakers,
   wherein, when the voice of the medical staff in charge is recognized from the voice recognition module while generating the play sound source as the output sound signal, the output signal generation module generates the output sound signal including a voice signal of the medical staff in charge.

2. The sound control system of claim 1, wherein the sound source stored in the sound source module comprises a plurality of basic sound sources, and the user interface further comprises a sound source mixing unit that allows the user to mix two or more basic sound sources from among the plurality of basic sound sources to generate a mixed sound source.

3. The sound control system of claim 2, wherein the sound source stored in the sound source module further comprises the mixed sound source.

4. The sound control system of claim 2, wherein the sound source mixing unit is capable of controlling a volume of each of the two or more basic sound sources to be mixed.

5. The sound control system of claim 1, further comprising a preprocessing module for preprocessing an electric sound signal transmitted from the microphone to transmit the electric sound signal to the voice recognition module, wherein the preprocessing module comprises a low pass filter (LPF) for outputting a primary processed signal in which high-frequency noise is reduced from the electric sound signal transmitted from the microphone, a speech enhancement for removing background noise from the primary processed signal to output a secondary processed signal, and a dynamic range compressor (DRC) for outputting a third processed signal in which voice intelligibility is enhanced from the secondary processed signal using a dynamic range compression technique.

6. The sound control system of claim 1, wherein the voice recognition module recognizes the voice of the medical staff in charge using deep learning.

7. The sound control system of claim 1, wherein the output signal generation module reduces the volume of the play sound source when the voice of the medical staff in charge is recognized from the voice recognition module while generating the play sound source as the output sound signal.

8. The sound control system of claim 1, wherein a control device including the voice recognition module, the sound source module, and the user interface is implemented by an application program installed in a portable communication terminal device.

9. A sound control system for dental treatment, the sound control system comprising:
   ear-worn speakers equipped to be worn by a patient in the dentist;
   a microphone that converts, into an electrical signal, a sound including a voice of a medical staff in charge of the patient;
   a preprocessing module for preprocessing an electric sound signal transmitted from the microphone to transmit the electric sound signal to the voice recognition module;
   a voice recognition module for recognizing the voice of the medical staff in charge from the preprocessed signal;
   a sound source module in which a plurality of sound sources including a plurality of basic sound sources for mental and physical stability of the patient and a mixed sound source in which two or more basic sound sources from among the plurality of basic sound sources are mixed, are stored;
   a user interface including a sound source selection unit that allows the patient to select a play sound source provided via the ear-worn speakers from among the plurality of sound sources, a sound source mixing unit for generating the mixed sound source and a setting unit; and
   an output signal generation module for generating an output sound signal output via the ear-worn speakers,
   wherein, when the voice of the medical staff in charge is recognized from the voice recognition module while generating the play sound source as the output sound signal, the output signal generation module generates the output sound signal including a voice signal of the medical staff in charge, and
   when the voice of the medical staff in charge is recognized from the voice recognition module while generating the play sound source as the output sound signal, the output signal generation module stops output of the voice signal of the medical staff in charge and increases a volume of the play sound source to restore the volume of the play sound source to the original state of the play sound source when a predetermined specific sound of the medical staff in charge is recognized in a state in which the volume of the play sound source is reduced and the play sound source is eliminated, and
   the sound source mixing unit generates the mixed sound source by mixing a plurality of basic sound sources selected by the patient through the sound source selection unit, and
   a volume of each of the plurality of basic sound sources selected to generate the mixed sound source by the sound source mixing unit is controlled, and
   the preprocessing module comprises a low pass filter (LPF) for outputting a primary processed signal in which high-frequency noise is reduced from the electric sound signal transmitted from the microphone, a speech enhancement for removing background noise from the primary processed signal to output a secondary processed signal, and a dynamic range compressor (DRC) for outputting a third processed signal in which voice intelligibility is enhanced from the secondary processed signal using a dynamic range compression technique, and
   a filtering frequency of the LPF is set by the setting unit, and
   the voice recognition module recognizes the voice of the medical staff in charge by using deep learning.

10. A sound control method for dental treatment using a sound control system for dental treatment including ear-worn speakers equipped to be worn by a patient in the dentist, a microphone that converts, into an electrical signal, a sound including a voice of a medical staff in charge of the patient, a voice recognition module for recognizing the voice of the medical staff in charge from an electrical sound signal input from the microphone, a sound source module that stores a plurality of sound sources for mental and physical stability of the patient, a user interface including a sound source selection unit that allows the patient to select a play sound source provided via the ear-worn speakers from among the plurality of sound sources, and an output signal generation module for generating an output sound signal output via the ear-worn speakers, the sound control method comprising:

- a sound source setting operation in which in which a play sound source provided to the ear-worn speakers is selected from among the plurality of sound sources through the user interface;
- a sound source outputting operation in which the play sound source selected in the sound source setting operation is output to the ear-worn speakers through the output signal generation module;
- a voice recognition checking operation in which it is checked whether the voice of the medical staff in charge is recognized through the voice recognition module while the play sound source is output in the sound source outputting operation; and
- a voice signal outputting operation in which the voice signal of the medical staff in charge is output to the ear-worn speakers through the output signal generation module when it is checked that the voice of the medical staff in charge is recognized in the voice recognition checking operation.

11. The sound control method of claim 9, wherein the sound source setting operation further comprises generating a mixed sound source by mixing two or more sound sources selected from among a plurality of sound sources through the user interface.

12. A sound control method for dental treatment using a sound control system for dental treatment including ear-worn speakers equipped to be worn by a patient in the dentist, a microphone that converts, into an electrical signal, a sound including a voice of a medical staff in charge of the patient, a low pass filter (LPF) for outputting a primary processed signal in which high-frequency noise is reduced from the electric sound signal transmitted from the microphone, a speech enhancement for removing background noise from the primary processed signal to output a secondary processed signal, and a dynamic range compressor (DRC) for outputting a third processed signal in which voice intelligibility is enhanced from the secondary processed signal using a dynamic range compression technique, as a preprocessed signal, a voice recognition module for recognizing the voice of the medical staff in charge from the preprocessed signal by using deep learning, a sound source module in which a plurality of sound sources for mental and physical stability of the patient are stored, a user interface comprising a sound source selection unit that allows the patient to select a play sound source provided to the ear-worn speakers from among the plurality of sound sources and a setting unit for setting a filtering frequency of the LPF, and an output signal generation module for generating an output sound signal output via the ear-worn speakers, the sound control method comprising:

- an operation in which the filtering frequency of the LPF is set by a setting unit;
- a sound source setting operation in which in which a mixed sound source is generated by mixing two or more sound sources selected by the patient from among a plurality of sound sources through the user interface and a play sound source provided to the ear-worn speakers is selected from among the plurality of sound sources and the mixed sound source;
- a sound source outputting operation in which the play sound source selected in the sound source setting operation is output to the ear-worn speakers through the output signal generation module;
- a voice recognition checking operation in which it is checked whether the voice of the medical staff in charge is recognized through the voice recognition module while the play sound source is output in the sound source outputting operation; and
- a voice signal outputting operation in which, when it is checked that the voice of the medical staff in charge is recognized in the voice recognition checking operation, the voice signal of the medical staff in charge is output to the ear-worn speakers through the output signal generation module in a state in which the volume of the play sound source is reduced and the play sound source is eliminated; and
- an operation in which, when a predetermined specific sound of the medical staff in charge is recognized in a state in which the volume of the play sound source is reduced and the play sound source is eliminated, performing of the voice signal outputting operation is stopped and the sound source outputting operation is performed to stop output of the voice signal of the medical staff in charge and to increase a volume of the play sound source to restore the volume of the play sound source to the original state of the play sound source, wherein, in the sound source setting operation, a volume of each of the two or more sound sources selected to generate the mixed sound source is controlled.

* * * * *